United States Patent
Ben-Ami et al.

(10) Patent No.: US 10,142,722 B2
(45) Date of Patent: Nov. 27, 2018

(54) AURAL MEASUREMENTS FROM EARPHONE OUTPUT SPEAKERS

(71) Applicant: Bugatone Ltd., Tel-Aviv (IL)

(72) Inventors: Edmund Ben-Ami, Beer-Shiva (IL); Noam Petrank, Tel Aviv-Yafo (IL)

(73) Assignee: Bugatone Ltd., Tel-Aviv (IL)

( * ) Notice: Subject to any disclaimer, the term of this patent is extended or adjusted under 35 U.S.C. 154(b) by 0 days.

(21) Appl. No.: 15/312,591

(22) PCT Filed: May 18, 2015

(86) PCT No.: PCT/IL2015/050525
§ 371 (c)(1),
(2) Date: Nov. 18, 2016

(87) PCT Pub. No.: WO2015/177787
PCT Pub. Date: Nov. 26, 2015

(65) Prior Publication Data
US 2017/0094401 A1    Mar. 30, 2017

Related U.S. Application Data

(60) Provisional application No. 62/000,626, filed on May 20, 2014.

(51) Int. Cl.
*H04R 1/10*   (2006.01)
*H04R 3/04*   (2006.01)
*H04R 3/00*   (2006.01)

(52) U.S. Cl.
CPC .............. *H04R 1/1091* (2013.01); *H04R 3/04* (2013.01)

(58) Field of Classification Search
CPC ...... H04R 1/1091; H04R 1/1075; H04R 3/00; H04R 3/04; H04R 2225/55; H04R 2400/01

(Continued)

(56) References Cited

U.S. PATENT DOCUMENTS 4,395,739 A    7/1983 Nakazawa et al.
5,159,936 A *  11/1992 Yelderman ............ A61B 1/227
                                              374/126

(Continued)

FOREIGN PATENT DOCUMENTS

CN    2162063    4/1994
EP    2202998    6/2010

(Continued)

OTHER PUBLICATIONS

European Search Report in European Application No. 14792178.7, dated Dec. 1, 2016, 4 pages.

(Continued)

*Primary Examiner* — Yogeshkumar Patel
(74) *Attorney, Agent, or Firm* — Fish & Richardson P.C.

(57) ABSTRACT

According to some embodiments of the present invention there is provided a method of using an earphone output speaker as a microphone for a phone call between two and/or more participants, or for measuring biometric data of a user. The method may comprise playing a received signal to an electro-acoustic output transducer of an earphone. The method may comprise instructing an audio processing circuit of a local client terminal to record an audio signal from the same electro-acoustic output transducer. The method may comprise calculating a voice signal and/or a biometric measurement based on a function combining the recorded audio signal, the received signal, and filtration coefficients, using a processing unit of the local client terminal. The method may comprise sending the voice signal and/or a biometric measurement through an output interface of the local client terminal.

26 Claims, 6 Drawing Sheets

(58) Field of Classification Search
USPC ............... 600/301, 300, 474, 500, 509, 549
See application file for complete search history.

(56) References Cited

U.S. PATENT DOCUMENTS

| | | | | |
|---|---|---|---|---|
| 5,919,143 | A * | 7/1999 | Jenkins | A61B 5/121 600/549 |
| 5,951,486 | A * | 9/1999 | Jenkins | A61B 5/121 600/559 |
| 6,126,614 | A * | 10/2000 | Jenkins | A61B 5/01 600/549 |
| 6,385,261 | B1 | 5/2002 | Tsuji et al. | |
| 7,065,219 | B1 | 6/2006 | Abe et al. | |
| 7,359,504 | B1 | 4/2008 | Reuss et al. | |
| 7,773,759 | B2 | 8/2010 | Alves et al. | |
| 8,249,265 | B2 | 8/2012 | Shumard | |
| 8,774,875 | B1 | 7/2014 | Halferty et al. | |
| 9,211,069 | B2 * | 12/2015 | Larsen | A61B 5/01 |
| 9,958,987 | B2 * | 5/2018 | Huppi | G06F 3/0418 |
| 2002/0133084 | A1 * | 9/2002 | Wilson | A61B 5/01 600/504 |
| 2004/0121796 | A1 * | 6/2004 | Peng | H04B 1/385 455/522 |
| 2004/0225207 | A1 * | 11/2004 | Bae | A61B 5/0002 600/340 |
| 2006/0128442 | A1 * | 6/2006 | Cho | H04M 1/6016 455/569.1 |
| 2007/0075965 | A1 * | 4/2007 | Huppi | H04M 1/72563 345/156 |
| 2007/0080817 | A1 * | 4/2007 | Grilliot | G08B 3/10 340/584 |
| 2007/0085157 | A1 * | 4/2007 | Fadell | G06F 3/0304 257/428 |
| 2007/0116314 | A1 * | 5/2007 | Grilliot | A62B 18/02 381/367 |
| 2007/0197881 | A1 * | 8/2007 | Wolf | A61B 5/0002 600/300 |
| 2007/0255115 | A1 * | 11/2007 | Anglin, Jr. | G06F 19/3418 600/300 |
| 2007/0265533 | A1 * | 11/2007 | Tran | A61B 5/021 600/481 |
| 2007/0273504 | A1 * | 11/2007 | Tran | A61B 5/0022 340/539.12 |
| 2007/0276270 | A1 * | 11/2007 | Tran | A61B 5/0022 600/508 |
| 2008/0001735 | A1 * | 1/2008 | Tran | G06F 19/3418 340/539.22 |
| 2008/0004904 | A1 * | 1/2008 | Tran | A61B 5/0006 705/2 |
| 2008/0006762 | A1 * | 1/2008 | Fadell | G01J 1/4204 250/201.1 |
| 2008/0044036 | A1 | 2/2008 | Konchitsky | |
| 2008/0140868 | A1 * | 6/2008 | Kalayjian | G06F 1/1698 710/8 |
| 2008/0146890 | A1 * | 6/2008 | LeBoeuf | A61B 5/0059 600/300 |
| 2008/0159555 | A1 | 7/2008 | Asada et al. | |
| 2008/0255430 | A1 * | 10/2008 | Alexandersson | A61B 5/02055 600/300 |
| 2009/0003617 | A1 | 1/2009 | Goldman et al. | |
| 2009/0003620 | A1 * | 1/2009 | McKillop | G06F 3/165 381/80 |
| 2009/0097689 | A1 * | 4/2009 | Prest | H04R 1/028 381/380 |
| 2009/0105548 | A1 * | 4/2009 | Bart | A61B 5/02438 600/300 |
| 2009/0131124 | A1 * | 5/2009 | Bibaud | H04M 1/6066 455/575.2 |
| 2009/0180631 | A1 * | 7/2009 | Michael | H04R 29/008 381/58 |
| 2009/0182526 | A1 * | 7/2009 | Quinn | G01J 5/0003 702/131 |
| 2009/0209303 | A1 * | 8/2009 | Kroll | H02J 7/025 455/575.2 |
| 2009/0245529 | A1 | 10/2009 | Asada et al. | |
| 2010/0069752 | A1 * | 3/2010 | Lewandowski | A61B 5/121 600/438 |
| 2010/0145203 | A1 | 6/2010 | Kim et al. | |
| 2010/0174390 | A1 | 7/2010 | Garrett et al. | |
| 2010/0195842 | A1 | 8/2010 | Sibbald et al. | |
| 2010/0217098 | A1 * | 8/2010 | LeBoeuf | A61B 5/00 600/301 |
| 2010/0228315 | A1 * | 9/2010 | Nielsen | A61B 5/0215 607/42 |
| 2010/0272276 | A1 | 10/2010 | Carreras et al. | |
| 2010/0296666 | A1 | 11/2010 | Lin | |
| 2010/0308999 | A1 * | 12/2010 | Chornenky | G08B 6/00 340/573.1 |
| 2011/0007907 | A1 | 1/2011 | Park et al. | |
| 2011/0137141 | A1 * | 6/2011 | Razoumov | A61B 5/0002 600/316 |
| 2011/0224493 | A1 * | 9/2011 | Oyadiran | A61B 1/00016 600/200 |
| 2011/0301435 | A1 | 12/2011 | Albert et al. | |
| 2012/0197093 | A1 * | 8/2012 | LeBoeuf | G16H 40/63 600/301 |
| 2012/0203077 | A1 * | 8/2012 | He | A61B 5/02055 600/301 |
| 2012/0242501 | A1 * | 9/2012 | Tran | A61B 5/0024 340/870.02 |
| 2012/0250873 | A1 | 10/2012 | Bakalos et al. | |
| 2013/0044887 | A1 * | 2/2013 | Dong | H04R 3/00 381/59 |
| 2013/0072807 | A1 * | 3/2013 | Tran | A61B 5/02405 600/485 |
| 2013/0095459 | A1 * | 4/2013 | Tran | A61B 5/6816 434/247 |
| 2013/0131519 | A1 * | 5/2013 | LeBoeuf | A61B 5/0077 600/476 |
| 2013/0172691 | A1 * | 7/2013 | Tran | A61B 8/488 600/301 |
| 2013/0195299 | A1 * | 8/2013 | Iseberg | A61B 5/7203 381/315 |
| 2013/0196721 | A1 | 8/2013 | Waterman et al. | |
| 2013/0208908 | A1 | 8/2013 | Theiler et al. | |
| 2013/0218022 | A1 * | 8/2013 | Larsen | A61B 5/01 600/474 |
| 2013/0245489 | A1 * | 9/2013 | Mullin | A61B 5/01 600/549 |
| 2013/0296685 | A1 * | 11/2013 | Tsuboi | A61B 5/01 600/407 |
| 2013/0343584 | A1 * | 12/2013 | Bennett | H04R 25/554 381/315 |
| 2013/0343585 | A1 * | 12/2013 | Bennett | H04R 25/554 381/315 |
| 2014/0018779 | A1 * | 1/2014 | Worrell | A61B 19/00 606/1 |
| 2014/0046192 | A1 * | 2/2014 | Mullin | H05K 13/00 600/474 |
| 2014/0051939 | A1 * | 2/2014 | Messerschmidt | A61B 5/0205 600/301 |
| 2014/0051940 | A1 * | 2/2014 | Messerschmidt | A61B 5/6803 600/301 |
| 2014/0073880 | A1 * | 3/2014 | Boucher | A61B 1/227 600/301 |
| 2014/0114147 | A1 * | 4/2014 | Romesburg | A61B 5/02416 600/301 |
| 2014/0128690 | A1 * | 5/2014 | LeBoeuf | A61B 5/02055 600/301 |
| 2014/0149065 | A1 * | 5/2014 | Pompei | G01K 13/002 702/131 |
| 2014/0194702 | A1 * | 7/2014 | Tran | A61B 8/06 600/301 |
| 2014/0266787 | A1 * | 9/2014 | Tran | A61B 5/0022 340/870.07 |
| 2014/0321682 | A1 * | 10/2014 | Kofod-Hansen | H04R 25/305 381/315 |

(56) References Cited

U.S. PATENT DOCUMENTS

| | | | |
|---|---|---|---|
| 2015/0011898 A1* | 1/2015 | Romesburg | A61B 5/02416 600/479 |
| 2015/0018636 A1* | 1/2015 | Romesburg | A61B 5/721 600/301 |
| 2015/0068069 A1* | 3/2015 | Tran | H04B 1/385 36/136 |
| 2015/0099941 A1* | 4/2015 | Tran | A61B 5/7214 600/300 |
| 2015/0125832 A1* | 5/2015 | Tran | G09B 19/0092 434/127 |
| 2015/0269825 A1* | 9/2015 | Tran | G08B 21/0446 340/539.12 |
| 2016/0063986 A1 | 3/2016 | Ben-Ami et al. | |
| 2016/0287166 A1* | 10/2016 | Tran | H04B 1/3827 |
| 2017/0188851 A1* | 7/2017 | LeBoeuf | A61B 5/02055 |

FOREIGN PATENT DOCUMENTS

| | | |
|---|---|---|
| EP | 2314212 | 4/2011 |
| WO | WO2000/10362 | 2/2000 |
| WO | WO2008/096125 | 8/2000 |
| WO | WO2012/167234 | 12/2012 |
| WO | WO 2012/167234 A1 * | 12/2012 |
| WO | WO 2014/178054 | 11/2014 |
| WO | WO 2015/166482 | 11/2015 |

OTHER PUBLICATIONS

International Preliminary Report on Patentability in International Application No. PCT/IL2014/050394, dated Nov. 3, 2015, 5 pages.
International Preliminary Report on Patentability in International Application No. PCT/IL2015/050525, dated Nov. 22, 2016, 6 pages.
International Search Report and Written Opinion in International Application No. PCT/IL2014/050394, dated Jul. 28, 2014, 9 pages.
International Search Report and Written Opinion in International Application No. PCT/IL2015/050525, dated Oct. 6, 2015, 10 pages.

* cited by examiner

AURAL MEASUREMENTS FROM EARPHONE OUTPUT SPEAKERS

This application is a National Stage Application under 35 U.S.C. 071 and claims the benefit of International Application No. PCT/IL2015/050525, filed May 18, 2015, which claims priority to U.S. Application No. 62/000,626, filed May 20, 2014, the disclosure of which is incorporated herein by reference.

BACKGROUND

The present invention, in some embodiments thereof, relates to measurements using earphone output speakers and, more specifically, but not exclusively, to temperature, biometric and/or acoustic measurements from an electro-acoustic output transducer of an earphone.

Physiological and environmental measurements may be performed by dedicated devices or by adding special sensors to accessory devices of client terminals. For example, glass analog and/or electronic digital thermometers are used for body temperature measurements. The device may be designed to measure body temperature from skin contact, or through the ear canal using infrared heat emission sensors. For example, special temperature sensors have been added to earphones for measuring temperature on a Smartphone while listening to music or participating in a voice call.

Personal use pulse rate monitors use pulse sensors and dedicated electronics to measure pulse rate when needed, or continually during exercise. The dedicated pulse rate sensors may be incorporated into chest bands, wrist bands, and earphones.

During voice conversations on cellular and/or cordless phones, a microphone is used to measure the voice signal of a participant in the call, and the signal is sent in real time to the other participant. An additional microphone may be used to reduce the background and/or Gaussian noise from the voice signal.

Earphones for mobile devices contain dedicated electro-acoustic output transducers, also referred to as earphone output speakers, to play music and/or voice signals from remote participants.

SUMMARY

According to some embodiments of the present invention there is provided a method of using an earphone output speaker as a microphone for a phone call between two or more participants. The method may comprise playing a received voice signal to one or more electro-acoustic output transducer of one or more earphone, wherein the received voice signal is a voice of a remote participant recorded from a remote client terminal. The method may comprise instructing an audio processing integrated circuit of a local client terminal to record a voice signal from the one or more electro-acoustic output transducer, wherein the voice signal is a voice of a local participant using the local client terminal. The method may comprise calculating a transmission voice signal based on a function combining the recorded voice signal, the received voice signal, and filtration coefficients, using a processing unit of the local client terminal. The method may comprise sending the transmission voice signal through an output interface of the local client terminal, thereby enabling acoustic voice playing of the transmission voice signal on the remote client terminal at a remote location for a phone call communication.

Optionally, the one or more electro-acoustic output transducer is an external speaker connected to an earphone.

Optionally, the one or more electro-acoustic output transducer is an internal speaker of the client terminal.

Optionally, the voice signal recording and the received voice signal playing are performed simultaneously from the same electro-acoustic transducer.

Optionally, the voice signal recording and the received voice signal playing are performed alternately from the same electro-acoustic transducer, where for a first time period playing is performed and for a second time period recording is performed in short enough time to be inaudible.

According to an aspect of some embodiments of the present invention there is provided a computer readable medium comprising computer executable instructions adapted to perform the methods described herein.

According to an aspect of some embodiments of the present invention there is provided a method of sending a noise reduced voice signal to a remote participant of a phone call between two or more participants. The method may comprise playing a received voice signal to one or more electro-acoustic output transducer of one or more earphone, wherein the received voice signal is a voice of a remote participant recorded from a remote client terminal. The method may comprise instructing an internal microphone integral to a local client terminal to record a voice signal, wherein the voice signal is a voice of a local participant using the local client terminal. The method may comprise instructing an audio processing integrated circuit of the local client terminal to record an aural audio signal using the one or more electro-acoustic output transducer. The method may comprise calculating a noise reduced voice signal based on a function combining the voice signal, the aural audio signal, the received voice signal and filtration coefficients, using a processing unit of the local client terminal. The method may comprise sending the noise reduced voice signal through an output interface, thereby enabling acoustic playing of the noise reduced voice signal on the remote client terminal at a remote location for a phone call communication.

Optionally, the aural audio signal recording and received voice signal playing are performed simultaneously from the same electro-acoustic output transducer.

According to an aspect of some embodiments of the present invention there is provided a method of presenting a pulse rate measurement. The method may comprise playing an output audio signal to one or more electro-acoustic output transducer of one or more earphone. The method may comprise instructing an audio processing integrated circuit of a client terminal to record an aural audio signal using the one or more electro-acoustic output transducer. The method may comprise calculating a pulse rate measurement based on a function combining the aural audio signal, the output audio signal, and filtration coefficients. The method may comprise presenting the pulse rate measurement.

Optionally, the aural audio signal recording and the output audio signal playing are performed simultaneously from the same one or more electro-acoustic output transducer.

Optionally, the aural audio signal recording and the output audio signal playing are performed alternately from the same one or more electro-acoustic output transducer, where for a first time period playing is performed and for a second time period recording is performed in short enough time to be inaudible.

Optionally, the electro-acoustic transducer is located inside an ear canal during recording of the aural audio signal.

Optionally, the pulse rate measurement is calculated based on measurement of a time shift between the aural audio signal and a second aural audio signal recorded from one or more second electro-acoustic output transducer.

Optionally, the pulse rate measurement is calculated based on a change in frequency response of an ear canal.

Optionally, the pulse rate measurement is presented to a user through a user interface.

Optionally, the pulse rate measurement is presented to a remote device through an output interface.

According to an aspect of some embodiments of the present invention there is provided a method of presenting a temperature measurement. The method may comprise playing an output audio signal to one or more electro-acoustic transducer. The method may comprise instructing an audio processing integrated circuit of a client terminal to record an audio signal using one or more electro-acoustic transducer. The method may comprise calculating two or more temperature measurements based on a function combining the audio signal, an output audio signal and filtration coefficients. The method may comprise presenting one or more of two or more temperature measurements.

Optionally, the One or More Electro-Acoustic Transducer is a Microphone.

Optionally, the one or more electro-acoustic transducer is an output speaker of an earphone.

Optionally, the one or more electro-acoustic transducer is an external speaker connected to an earphone, and two or more temperature measurement comprises ambient and inner ear temperature measurements.

Optionally, the one or more electro-acoustic transducer is an internal speaker of a client terminal, and two or more temperature measurement comprises ambient and device temperature measurements.

Optionally, the electro-acoustic transducer is located inside an ear canal of a target user during recording of the audio signal and one of two or more temperature measurements is an inner ear measurement correlated with a body temperature of the target user.

Optionally, one or more of two or more temperature measurement is presented to a user through a user interface.

Optionally, one or more of two or more temperature measurement is presented to a remote device through an output interface.

According to an aspect of some embodiments of the present invention there is provided a computer program product for sending a transmission voice signal. The computer program product may comprise a computer readable storage medium. The computer program product may comprise first program instructions to play a received voice signal to one or more electro-acoustic output transducer of one or more earphone. The computer program product may comprise second program instructions instruct an audio processing integrated circuit of a local client terminal to record a voice signal using the one or more electro-acoustic output transducer. The computer program product may comprise third program instructions to calculate a transmission voice signal based on a function combining the recorded voice signal. The computer program product may comprise fourth program instructions to send the transmission voice signal through an output interface of the local client terminal, and the first, second, third, and fourth program instructions may be stored on the computer readable storage medium.

According to an aspect of some embodiments of the present invention there is provided a computer program product for sending a noise reduced voice signal. The computer program product may comprise a computer readable storage medium. The computer program product may comprise first program instructions to play a received voice signal to one or more electro-acoustic output transducer of one or more earphone. The computer program product may comprise second program instructions instructing an internal microphone integral to a client terminal to record a voice signal. The computer program product may comprise third program instructions to instruct an audio processing integrated circuit of the client terminal to record an aural audio signal using one or more electro-acoustic output transducer. The computer program product may comprise fourth program instructions to calculate a noise reduced voice signal based on a function combining the voice signal, the aural audio signal and filtration coefficients. The computer program product may comprise fifth program instructions to send the noise reduced voice signal through an output interface of the client terminal, and the first, second, third, fourth, and fifth program instructions are stored on the computer readable storage medium.

According to an aspect of some embodiments of the present invention there is provided a computer program product for presenting a pulse rate measurement. The computer program product may comprise a computer readable storage medium. The computer program product may comprise first program instructions to play an output audio signal to one or more electro-acoustic output transducer of one or more earphone. The computer program product may comprise second program instructions instruct an audio processing integrated circuit of a client terminal to record an aural audio signal using one or more electro-acoustic output transducer. The computer program product may comprise third program instructions to calculate a pulse rate measurement based on a function combining the recorded aural audio signal. The computer program product may comprise fourth program instructions to present the pulse rate measurement, and the first, second, third, and fourth program instructions are stored on the computer readable storage medium.

According to an aspect of some embodiments of the present invention there is provided a computer program product for presenting a temperature measurement. The computer program product may comprise a computer readable storage medium. The computer program product may comprise first program instructions to play an output audio signal to one or more electro-acoustic output transducer of one or more earphone. The computer program product may comprise second program instructions instruct an audio processing integrated circuit of a client terminal to record an aural audio signal using one or more electro-acoustic output transducer. The computer program product may comprise third program instructions to calculate a temperature measurement based on a function combining the recorded aural audio signal. The computer program product may comprise fourth program instructions to present the temperature measurement, and the first, second, third, and fourth program instructions are stored on the computer readable storage medium.

According to an aspect of some embodiments of the present invention there is provided a device for sending a voice signal to a remote participant in a phone conversation. The device may comprise an interface for sending a local voice signal of a local participant in the phone conversation and receiving a remote voice signal of a remote participant. The device may comprise an audio socket for connecting an earphone to the device. The device may comprise one or more storage units with sets of processor instructions for performing the action of playing a received voice signal to one or more output speaker of one or more earphone. A storage unit may comprise sets of processor instructions for performing the action of instructing an audio circuit to record an aural signal from the one or more output speaker of the earphone A storage unit may comprise sets of processor instructions for performing the action of computing the local voice signal from the aural signal A storage unit may comprise sets of processor instructions for performing the action of sending the local voice signal to a player device of the remote participant in the phone conversation. The device may comprise one or more processing unit configured for retrieving the sets of processor instructions from the one or more storage unit, and executing the sets of processor instructions.

Optionally, the device comprises a microphone, the microphone records a second voice signal, the voice signal is a noise reduced voice signal computed using the aural signal and the second voice signal.

According to an aspect of some embodiments of the present invention there is provided a device for presenting a biometric measurement. The device may comprise an audio socket for connecting an earphone to the device. The device may comprise one or more storage unit containing sets of processor instructions for playing an output audio signal to one or more output speaker of one or more earphone. A storage unit may contain sets of processor instructions for instructing an audio circuit to record an aural signal from the one or more output speaker of the earphone. A storage unit may contain sets of processor instructions for computing one or more biometric measurement from the aural signal. A storage unit may contain sets of processor instructions for presenting the one or more biometric measurement. The device may comprise one or more processing unit configured for retrieving the sets of processor instructions from the one or more storage unit, and executing the sets of processor instructions.

Optionally, the device comprises a data interface, and the one or more biometric measurement is presented on a remote device using the data interface.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention may involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
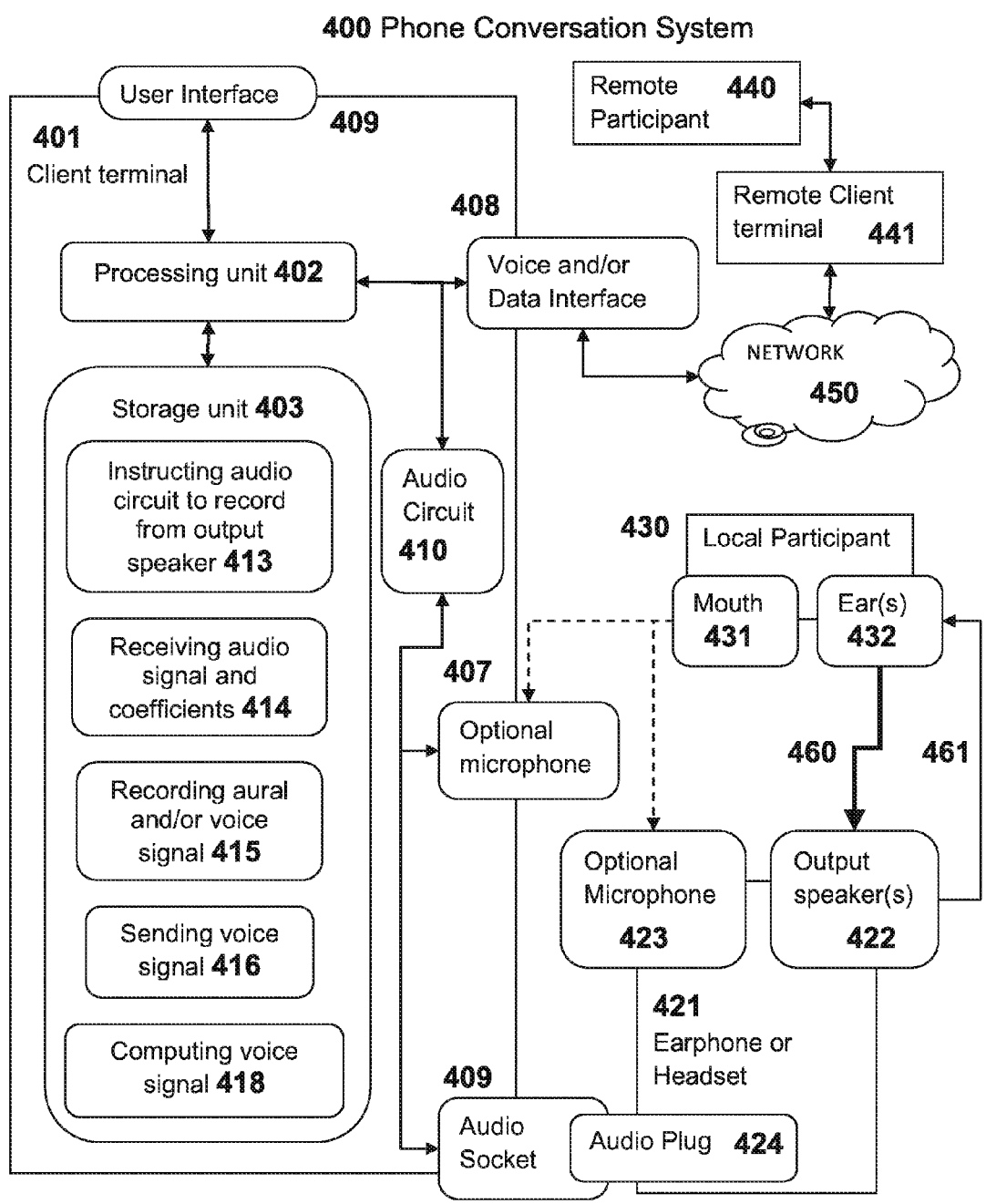
FIG. 1A is a schematic illustration of a system and device to calculate an, optionally noise reduced, voice signal from an earphone output speaker, according to some embodiments of the invention.

The present invention, in some embodiments thereof, relates to measurements using earphone output speakers and, more specifically, but not exclusively, to temperature, biometric and/or acoustic measurements from an electroacoustic output transducer of an earphone.

Current methods for biometric and aural sound measurements require dedicated hardware and electronics, increasing the product cost, development time and development costs. Additionally, some of these methods may require the user to be stationary during measurements as the measurement devices are sensitive to background noise and subject motion.

To overcome these limitations, one or more output speakers of earphones may be used for making measurements while the user is listening to music, soundtrack, a voice of a phone conversation, and the like using the same output speakers. An audio processing circuit of a client terminal, optionally with a rewiring adaptor, may be configured to record an aural sound signal from the earphone electroacoustic output transducer, such as an earphone output speaker. For example, the earphones and client terminal are off-the-shelf products, with no special hardware incorporated into the client terminals. The aural sound signal may be processed by the processor of the client terminal to produce measurements of temperature, pulse rate, noise signal, and voice signal. As used herein, the term client terminal means a smartphone, a mobile phone, a portable music player, a tablet, a laptop, a wearable device, a personal computer, and the like. As used herein, the term earphone refers to earphones, headphones, earbuds and the like, comprising at least one output speaker, such as an electro-acoustic transducer. The earphones can be regular earphones used for everyday voice conversations and music playing, and do not require special sensors or hardware.

For example, the aural sound signal can be used to compute a voice signal for use in a phone conversation with a remote participant. In another example, the client terminal and/or earphone have an integrated microphone, and the aural sound signal can be used to compute a noise-reduced voice signal for a phone conversation. In another example, the acoustic characteristics of the aural sound signal are sensitive to the temperature of the inside and outside of the earphone electro-acoustic output transducer. In this example, processing the aural sound signal with dedicated methods allows computing temperature measurements for the inner ear and surroundings. In another example, analyzing the periodic features of one or more aural sound signals allows computing a pulse rate.

For example, using existing thermometer devices require the subject to be relatively stationary and may not be capable of monitoring the temperature for long periods of time during normal daily activities. Using some embodiments of the methods described herein, an earphone output speaker may be used to measure the body temperature conveniently and continuously, enabling application of body temperature monitoring for fertility uses, healthy monitoring, emotional monitoring, and/or other uses. Using an aural sound signal recorded from the output speaker internal to the client terminal allows measuring the temperature of the client terminal and determines the power usage based on the temperature measurement. If the client terminal transceiver, processor and display usage do not account for the power usage, the client terminal may be malfunctioning. The recorded aural sound signal is recorded from the same speakers used for playing music and/or listening to a voice signal during a phone conversation.

According to some embodiments of the present invention there is provided computerized methods and devices, for using earphone output speakers to record aural acoustic signals and convert these signals to measurements of the environment of the earphone output speakers. The client terminal devices may have an audio processing integrated circuit, or as referred to herein as a coder/decoder (CODEC), that may be configured to allow signal recording from the same earphone output speakers used for playing music. As used herein, the term CODEC means an audio processing integrated circuit which may comprise a circuit or integrated circuit used to process the input and output of audio signals of the client terminal. The aural acoustic signal may be processed using the client terminal to compute measurements relating to the output speakers environment. For example, the aural acoustic signal is processed to produce a voice signal of the owner of the mobile client terminal for use in a phone conversation, even when no microphone is connected to the CODEC. For example, the acoustic signal is used to produce a noise reduced voice signal from a voice signal collected from a microphone. For example, the aural acoustic signal is used to compute a heart sound from an earphone output speaker located near and/or internal to the ear canal. For example, the acoustic signal is used to compute a heart rate from an earphone output speaker located near and/or internal to the ear canal. For example, the aural acoustic signal is used to compute a body temperature from an earphone output speaker located near and/or internal to the ear canal. For example, the aural acoustic signal is used to compute an ambient temperature from an earphone output speaker.

Optionally, a rewiring adapter is used to enable the CODEC to record an aural audio signal from the earphone output speakers.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1A, which is a schematic illustration of a system 400 and device 401 to calculate a voice signal, optionally noise reduced, from an earphone output speaker 460, according to some embodiments of the invention. In some embodiments, a client terminal device 401 may contain a user interface 409, a processing unit 402, an audio circuit 410, a voice and/or data interface 408, and an audio socket 409. The user interface 409 may be used to control the operation of the device, issue command, such as to initiate a phone call, and to see the calculated results of the methods. One or more audio sockets 409 may be used to connect one or more audio plugs 424 of earphones 421 to the client terminal 401.

The processing unit 402 may be configured to retrieve processor instructions from a storage unit 403, controlling the audio circuit 410, and transferring data to or from the interfaces. The storage unit 403 may contain processor instructions for configuring an audio circuit 410, also referred to as an audio processing integrated circuit, to record from an earphone output speaker 413, thus enabling the recording of an aural audio signal from earphone output speakers. For example, the aural signal 460 is recorded from the ear(s) 432 of the local phone conversation participant 430 using an earphone 421 output speaker 422, while an output voice signal of the remote participant 461 is being transmitted to the same ear(s) 432. The storage unit 403 may further contain processor instructions for receiving an output audio signal 414 to be played on the earphone output speaker 461, such as the voice signal from a remote participant 440 in phone conversation. The recording is performed from the same output speakers used to play the remote participant voice signal. The storage unit 403 may further contain processor instructions for recording 415 an aural audio signal 460 from the output earphones. The storage unit 403 may further contain processor instructions for computing a voice signal 418 of the local participant 430 from the aural audio signal 460, such that the voice signal is suitable for sending to a remote participant 440 in a phone conversation. Optional, the storage unit 403 may further contain processor instructions for recording a direct voice signal 415 from a microphone, as at 407. Optionally, the storage unit 403 may further contain processor instructions to calculate a noise reduced voice signal 418 based on the aural voice signal, direct voice signal, and filtration coefficients. Optionally, the storage unit 403 may further contain processor instructions to send the noise reduced voice signal to the remote participant 440 of the phone conversation. Optionally, the microphone is part of the earphone 423, such as a headset. The storage unit 403 may further contain processor instructions for sending a voice signal 416, optionally noise reduced, to a remote client terminal 441.

The device may comprise and a voice and/or data interface 408 for placing a phone conversation with a remote client terminal 441 through a network 450, such as a cellular and/or Ethernet network. The device may be connected to an earphone 421 and the earphone may contain one or more output speakers 422 and one or more optional microphones 423.

Figure 1B:
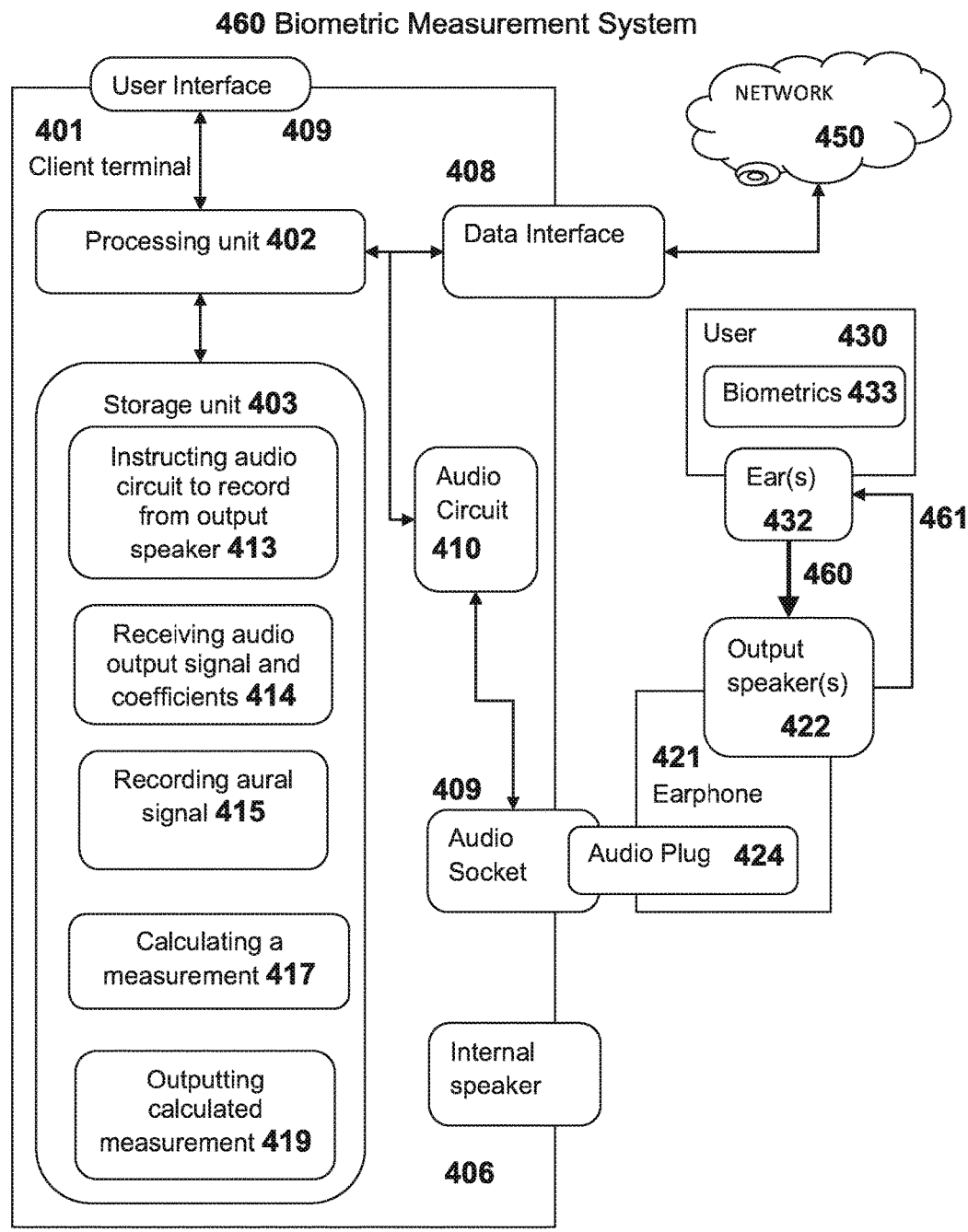
FIG. 1B is a schematic illustration of a system and device to calculate a pulse and/or temperature measurement from an aural signal recorded from an earphone output speaker, according to some embodiments of the invention.

Reference is now made to FIG. 1B, which is a schematic illustration of a system 460 and device 401 to calculate a pulse and/or temperature measurement from an aural signal recorded from an earphone output speaker, according to some embodiments of the invention. In some embodiments, a client terminal device 401 may contain a user interface 409, a processing unit 402, a storage unit 403, an audio circuit 410, and an audio socket 409. The user interface 409 may be used to control the operation of the device, issue command, such as to request a pulse and/or temperature measurement, and to see the calculated result. An audio socket 409 may be used to connect one or more audio plugs 424 of earphones 421 to the audio circuit 410 of the client terminal 401.

The storage unit 403 may contain processor instructions for instructing 413 an audio circuit 410, also referred to as an audio processing integrated circuit, to record an aural signal from an earphone 421 output speaker 422. The storage unit 403 may further contain processor instructions for receiving an output audio signal 414 to be played on the earphone 421 output speaker(s) 422, such as a music signal to be played 461 while performing the aural signal recording and calculating biometric measurements. The storage unit 403 may further contain processor instructions for recording 415 an aural signal 460 from the earphone 421 output speaker(s) 422. The storage unit 403 may further contain processor instructions for calculating biometric measurements 417 based on the aural audio signal 460, such as pulse rate and temperature measurements. The storage unit 403 may further contain processor instructions for outputting biometric measurement data 419 to a client terminal 401 user interface 409. Optionally, a data interface 408 may be used to output the biometric measurements to a remote storage and/or display on a network 450, such as in tele-monitoring of biometric data.

Optionally, the client terminal 401 may also contain one or more internal output speakers 406 for measuring the intern temperature of client terminal and/or the ambient temperature of the client terminal surroundings.

Both the system for phone conversations 400 and the system for biometric measurements 460 may comprise a large portion of system components in common. For example, the client terminal 401 and earphones 421 may be the same hardware, applied to different use cases and using different calculations. For example, the client terminal 401 and earphones 421 are both off-the-shelf products with no special hardware technical features.

According to some embodiments of the present invention there are provided computerized methods, for using earphones for noise reduction in voice conversations, and/or to use earphones as a microphone in voice conversations.

Figure 2:
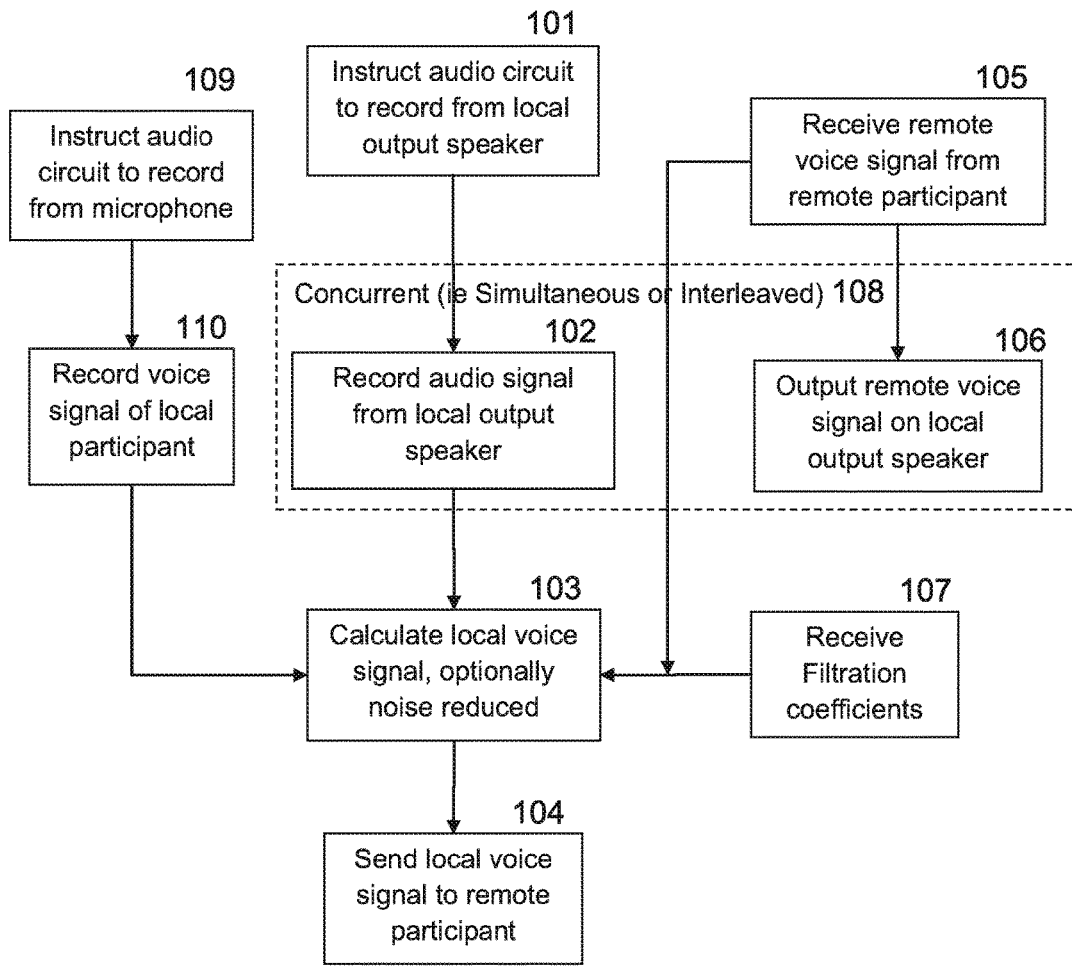
FIG. 2 is a flowchart of a method to generate a phone conversation audio signal from an earphone output speaker, according to some embodiments of the invention.

Reference is now made to FIG. 2, which is a method to generate a phone conversation voice signal from an earphone output speaker, according to some embodiments of the invention. The computerized processing unit 402 of a client terminal 401 may instruct an audio processing integrated circuit 410 to record 101 from an earphone 421 output speaker 422. A remote voice signal is received 105 by the local client terminal 401 from a remote client terminal 441 of the remote participant 440 in the phone conversation and played 106 on the earphone output speaker 461. Concurrent with the remote voice signal output on the earphones 421, an aural audio signal is recorded 102 from the local earphone 421 output speaker 422. After receiving filtration coefficients 107, the recorded audio and separately received remote voice signal may be used to calculate the local voice signal 103 by a processing unit 402. This local voice signal is then sent by a processing unit 402 to the remote participant client terminal 104, thus enabling a voice signal without using a microphone connected to the local client terminal device.

When the local client terminal 401 has an attached microphone, the method may be used to send a noise reduced local voice signal to the remote terminal 104 by a processing unit 402. A computerized processing unit 402 instructs an audio processing circuit 410 to record 109 a voice signal of the local participant from the microphone 407, and then records 110 the local participant's voice signal from the microphone 407. The recorded voice signal is used with the filtration coefficients 107, remote voice signal 105, and the recorded audio signal 460 from the local earphone 421 output speaker 422 to calculate 103 a noise reduced local voice signal by a processing unit 402, which is sent 104 by a processing unit 402 to the remote participant client terminal 441.

According to some embodiments of the present invention there are provided computerized methods, for recording heart sounds and/or measuring pulse rate using the same earphones output speakers used for playing audio signals.

Figure 3:
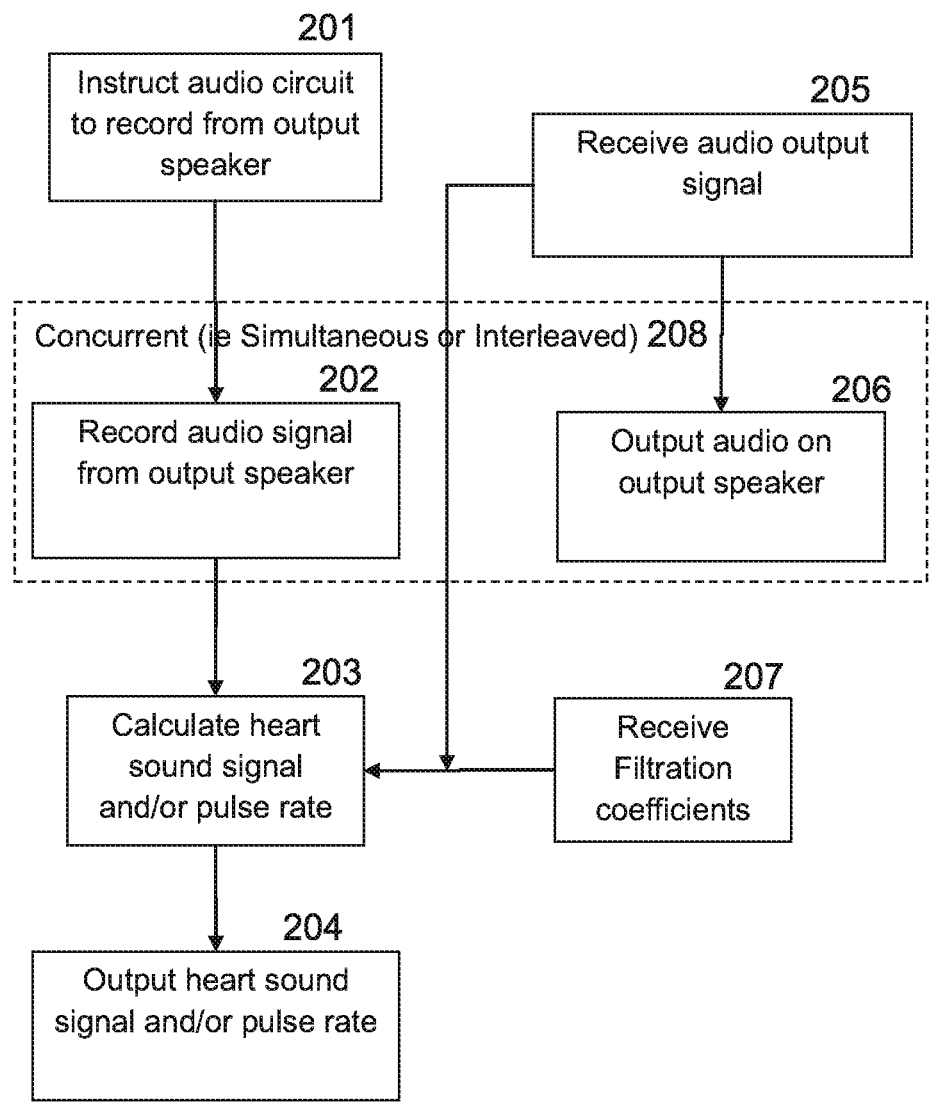
FIG. 3 is a flowchart of a method to measure a pulse rate from an earphone output speaker, according to some embodiments of the invention.

Reference is now made to FIG. 3, which is a flowchart of a method to measure a pulse rate from an earphone 421 output speaker 422, according to some embodiments of the invention. A processing unit 402 instructs the audio circuit 410 to record 201 an audio signal from an earphone output speaker 422, and subsequently records 202 the audio signal from the earphone output speaker. A previously received audio signal 205 may be outputted concurrently 206 on the earphone output speaker 422, as at 461. After receiving filtration parameters 207, the recorded audio and received audio output signal are used by a processing unit 402 to calculate the heart sound signal and/or pulse rate 203. The heart sound signal and/or pulse rate are outputted 204 by a processing unit 402 to a user interface 409 and/or to a remote device through a data interface 408 and the internet 450.

According to some embodiments of the present invention there are provided computerized methods, for measuring temperature using an output audio transducer, such as one or more earphone output speakers.

Figure 4:
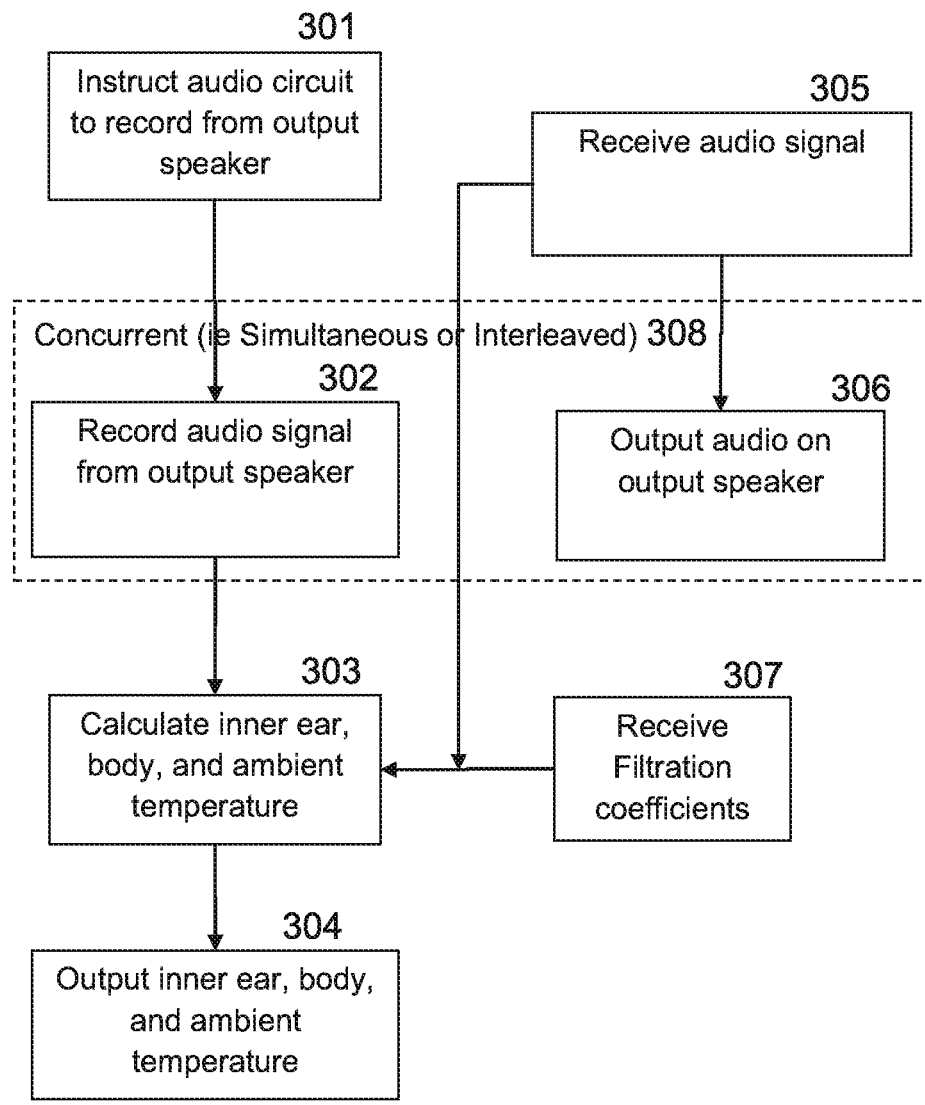
FIG. 4 is a flowchart of a method to measure temperature from an earphone output speaker, according to some embodiments of the invention.

Reference is now made to FIG. 4, which is a flowchart of a method to measure temperature from an earphone output speaker 422, according to some embodiments of the invention. A processing unit 402 instructs the audio circuit 410 to record 301 an audio signal from an earphone 421 output speaker 422, and subsequently records 302 the audio signal from the earphone output speaker as at 460. A previously received audio signal 305 may be outputted by a processing unit 402 concurrently, for example simultaneously or interleaved, on the earphone output speaker 306. After receiving filtration parameters 307, the recorded audio and received audio output signal are used by a processing unit 402 to calculate the temperature data of the inner ear, user's body and ambient surroundings of the earphone output speaker 303. The temperature data is then outputted 304 by a processing unit 402 to a user interface 409 and/or to a remote device through a data interface 408 and the internet 450.

According to some embodiments of the present invention there are provided computerized methods, for a client terminal to receive input from a microphone and/or acoustic output transducers of earphones. The methods may be used if the audio processing circuit may be configured to use the earphones as an input source to record the sounds within the ear space either simultaneously or interleaved. The calculated signal may be a voice signal even though there is no microphone connected to the client terminal. For example, the output speakers of earphones are used to record a voice signal for a phone call application.

The recorded signal from the earphones may be used to calculate a voice signal, optionally together with input from the microphone to produce a reduced noise voice signal.

Optionally, a background signal is collected from one or more speaker of the earphones.

Optionally, a voice conversation is enabled in smartphones using only earphones, without a connected microphone. For example, a music player as a client terminal without an internal microphone and/or without an earphone microphone participates in a phone conversation using a WiFi™ data connection using the earphone output speakers as a microphone. In this example, the music player is configured to record the aural signal and compute a voice signal for sending to the remote participant of the phone conversation.

According to some aspects of embodiments of the invention, the method configures an audio circuit to connect an input path from the earphones to the audio processing circuit of the client terminal. The method may allow either alternating or simultaneous recording from one or both output speakers of the earphones. For example, alternating recording may be done during short intervals while the output signal to the speakers is stopped, such that the listener does not hear a break in the speaker acoustic output. For example, simultaneous recording may be done concurrently with an audio output signal being played from the earphone output speakers. For noise reduction applications, the method may allow receiving input from an optional microphone.

For example, reference is now made to an exemplary function for calculating a noise reduction signal. For brevity, the following are defined:

E denotes an input signal vector recorded from output earphone(s) speaker(s);

A denotes an output audio signal vector transmitted to the earphone(s), where A=0 if the recording is interleaved;

M denotes an input signal vector recorded by microphone(s);

$Ce[N_1]$ denotes earphone(s) output coefficients, a vector of $N_1$ number of elements;

$Ve[N_2]$ denotes earphone(s) translation constants, calibrated per user and earphone(s), a vector of $N_2$ number of elements;

$Cf[N_3]$ denotes filtration coefficients, a vector of $N_3$ number of elements; and T denotes a microphone noise reduction coefficient vector.

When there is no microphone input, a voice signal may be calculated using a function such as $Ve*Cf*(E-Ce*A)$, where * denotes the convolution function.

Optionally, input is collected from two or more earphones and E denotes the average input signal. For example, $E_1$ is collected from the left earphone and $E_2$ is collected from the right earphone, and E denotes the average of $E_1$ and $E_2$.

Optionally, $N_1$, $N_2$ and $N_3$ have different values. These different values correspond to different frequency response functions of the different filter coefficient vectors.

For example, when an audio output signal A is sent to be played by the earphones, the acoustic audio output of the earphones is $C_e*A$.

For example, when E is the audio signal recorded inside the ear from the earphone output speakers, $K=V_e*E$ is the speech signal sound.

For example, filtration coefficients implement a weight function on the frequencies, where a weight of 0 is applied to the low frequencies for which the skull doesn't block outside noise well and applied to frequencies which are outside the speech spectrum. Non-zero weights are applied to frequencies inside the speech spectrum for which the skull blocks outside noise.

When a voice signal is collected from a microphone, the noise reduced voice signal may be calculated using the function $T*Cf*M$.

The coefficients T may be recalculated for a time period, for example, 0.1 seconds. T may be calculated from the equation:

$$T = \mathrm{argmin}_T(\|T*M - V_e*C_f*(E-C_e*A)\|^2)$$

where argmin is defined as the value of the given argument, T in this example, for which the function in parentheses attains its minimum value.

This function may find the best noise reduction filter that correlates between the earphone and microphone recordings of a voice signal. Similarly, the two recordings may be used to also find background noises that may be reduced from the microphone recordings. For example, background white noise is reduced from the microphone recording. For example, a repetitive background noise is reduced from the microphone recording, such as a train and/or other motor vehicle noise. For example, a noise reduced voice signal may be calculated using the equation $M - V_e*C_f*(E-C_e*A)$.

Optionally, the cross-correlation is computed between two audio signals to find background sounds, and the background sounds removed from an audio signal that comprises a voice signal, resulting in the voice signal being more audible.

Optionally, a cost function is minimized to find T using mathematical optimization. For example, the minimum of a cost function $\|T*M - V_e*C_f*(E-C_e*A)\|^2$ may be found using iterative methods, heuristic methods, and/or by solving corresponding linear equations. For example, the cost function minimum may be found using a simplex method, a least squares method, a newton-raphson method, a simulated annealing method, a combinatorial algorithm, and the like.

According to some embodiments of the present invention there are provided computerized methods, for a client terminal to measure heart pulse rate using these audio output transducers while these audio output transducers are inside or tightly placed over the user's ear(s). For example, the output transducers may be used instead of microphones to record the acoustic signals from the blood pulse in the ears, and the signal is used to calculate a heart pulse rate.

Optionally, the acoustic recording from the output audio transducer is either simultaneous or interleaved (alternating) with the playing of an audio signal from the same output audio transducer.

Optionally, the acoustic recording is performed from the transducer of one ear, from both ears separately, or from both ears together.

Optionally, three phenomena may be used to estimate the user's pulse rate.

The first phenomenon is that venous pulse may be audible inside the ear. This phenomenon may be used by assuming that the audio recorded inside and/or adjacently to the ear may be modeled by a signal P+N where P is the venous pulse signal and N is noise signal. When the recording is performed while transmitting an audio output signal then N may be the sum of transmitted audio, noise from the sound card, and white noise. When the recording is interleaved then N may only be the sum of noise from the sound card and white noise.

The subscripts 1 and 2 of the signals $P_1$ and $P_2$ denote the venous pulse signals in each of two ears. These signals are similar and include a time shift due to the different flow paths from the heart to the arteries of each ear.

The second phenomenon that may be used to calculate pulse rate is that the time shift between $P_1$ and $P_2$ may be inversely proportional to the pulse rate. Hence, finding the time shift between $P_1$ and $P_2$ may determine pulse rate, since it may have a linear relationship with the time shift under certain conditions for a specific person in a small enough time interval. This linear relationship may be more complicated when the person's parameters, such as age, height, weight, and sex, are not assumed. This linear relationship may be more complicated when the pulse value range varies during the measurement period. Optionally, the non-linear aspects of the relationship between time shift and pulse rate are calibrated specifically for each individual.

The third phenomenon used to measure the pulse rate is that changes in the blood pressure may cause changes in the volume of the ear canal. The blood pressure may be inversely proportional to the volume of the ear canal. Thus, calculating the changes in the ear canal volume may be used to deduce the blood pressure wave. Any changes in the volume of the ear canal may change the frequency response of the ear canal. Calculating the ear canal frequency response may be done by simultaneously playing and recording an audio signal from a transducer inside and/or tightly placed over the ear.

For example, reference is now made to exemplary functions for calculating a pulse rate from an audio signal. For example, functions ALG. 1 and ALG. 2 use the first phenomenon while functions ALG. 3 and ALG. 4 use the second phenomenon. When input signals from each of both ears are recorded, functions ALG. 1 and ALG. 3 may be used to find the pulse rate. When input from only one ear is recorded, then function ALG. 1 may be used to find the pulse rate. When the sum of recorded inputs from both ears is known than functions ALG. 2 and ALG. 4 may be used to find the pulse rate. Optionally, a number of functions and/or algorithms are used and the average result outputted. For example, function ALG. 5 uses the third phenomenon to calculate a pulse rate.

Functions for calculating a pulse rate from an audio signal may use a windowed autocorrelation function to find patterns of similarity in the recorded audio signal from the output transducer. These windowed autocorrelation functions may find the repetitive heart beat sound in the recorded audio signal by searching for the repeating patterns of a segment of the audio recording.

For brevity, the following are additionally defined:

Ce[ ] denotes transducer coefficients vector

A[ ] denotes an output audio signal vector transmitted by the transducer $CV_{sc}$[ ][ ] denotes a covariance matrix of the sound card noise W denotes a window interval length for pulse rate measurement $D_r$ denotes a number of samples corresponding to 0.1 of one heart beat period E[ ] denotes an input signal vector from an output transducer $S_d$ denotes a number of samples corresponding to shift between $P_1$ and $P_2$ where d is number of samples per heart beat R[ ][ ] denotes an r×r matrix such that $CV_{sc}$=RR'

$$TC[\ ][\ ] \text{ denote the } t \times t \text{ matrix equal to } \begin{pmatrix} R \\ I \\ -R \\ -I \end{pmatrix} (R'I - R' - I)$$

$E_1$[ ] and $E_2$[ ] denote input signal vectors from the individual transducers E[ ] may denote the sum of signals from both transducers fr denotes audio signal sample rate in samples per second hr denotes the heart rate in beats per minute hr=60×fr/(10× $D_r$)

Optionally, ALG. 1 finds the pulse rate from an audio signal modeled by $E=P_i+N_i$ when $N_i$ is the sum of transmitted audio, noise from the sound card, and white noise. In this model E may be an audio signal from either of the ears. Only the overall length of the signal matters.

Let F=E−Ce*A, and the operator z[x,y] denotes the subvector of z between indices x and y inclusive. For example, $F_1=E_1-Ce*A_1$ and $F_2=E_2-Ce*A_2$. The correlation function in this example is:

$$Y_{i,j}=F[i \cdot W,(i+1) \cdot W]-F[i \cdot W+j,(i+1) \cdot W+j]$$

In this example, hr is calculated for hr values between 50 and 150 using the cost function:

$$\Sigma_{i=1} \; {}_{T}TC^{-1}Y_{i,j}[k,k+t]}^{M\Sigma_{j=9Dr,9Dr+1,\ldots,11\,Dr}\Sigma_{k=1,\ldots,W-t}Y_{i,j}[k,k+t]} \qquad \text{ALG. 1}$$

where M=length(E)/W, and the output is the value of hr corresponding to the maximal value of the cost function ALG. 1, taking into account the relationship between $D_r$ and hr.

For example, sampling rate is 44 KHz, of 44,000 samples per second, signal is measured for 10 seconds, and heart rate is 1 beat per second or 44,000 samples per heart beat (d). So total samples is 10*44,000=440,000. Dr is 4,400, and j may have values from 9*4,400 (39,600) to 11*4,400 (48,400). Given a W equivalent to 3 pulses (=3 seconds) then W=3*44,000=132,000 and i may have values from 1 to 3.

Optionally, ALG. 2 finds the pulse rate from an audio signal modeled by $E=P_1+P_2+N$, where N denotes the sum of transmitted audio from both ears, noise from the sound card, and white noise.

The correlation function in this case is:

$$Y_{i,j}=F[i \cdot W,(i+1) \cdot W]-F[i \cdot W+j,(i+1) \cdot W+j]$$

In this example, hr is calculated for hr values between 50 and 150 using the cost function:

$$\Sigma_{i=1\ldots M}\Sigma_{j=9Dr,\ldots 11\,Dr}(\Sigma_{k=1,\ldots,W-t}Y_{i,j}[k,k+t]^T TC^{-1}Y_{i,j}[k,k+t])(\Sigma_{k=1,\ldots,W-t}Y_{i,j}[S_j+k,S_j+k+t]^T TC^1 Y_{i,j}[S_j+k,S_j+k+t]) \qquad \text{ALG. 2}$$

and the output is the value of hr corresponding to the maximal value of the cost function ALG. 2, taking into account the relationship between $D_r$ and hr.

Optionally, ALG. 3 finds the pulse rate from an audio signal modeled by $E_1=P_1+N_1$ and $E_2=P_2+N_2$, where $N_i$ denotes the sum of transmitted audio, noise from the sound card, and white noise for each ear.

The correlation function in this example is:

$$Z_{i,j}=F_1[i \cdot W,(i+1) \cdot W]-F_2[\cdot W+j,(i+1) \cdot W+j]$$

In this example, hr is calculated for hr values between 50 and 150 using the cost function:

$$\Sigma_{i=1\ldots M}\Sigma_{j=9\,Dr,\ldots 11Dr}\Sigma_{k=1,\ldots W-t}Z_{i,Sj}[k,k+t]^T TC^{-1}Z_{i,Sj}[k,k+t] \qquad \text{ALG. 3}$$

and the output is the value of hr corresponding to the maximal value of the cost function ALG. 3, taking into account the relationship between $D_r$ and hr.

Optionally, ALG. 4 finds the pulse rate from an audio signal modeled by $E=P_1+P_2+N$, where N denotes the sum of transmitted audio, noise from the sound card, and white noise.

The correlation function in this case is:

$$Y_{i,j}=F[i\cdot W,(i+1)\cdot W]-F[\cdot W+j,(i+1)\cdot W+j]$$

In this example, hr is calculated for hr values between 50 and 150 using the cost function:

$$\Sigma_{i=1\ldots,M}\Sigma_{j=9Dr,\ldots,11Dr}(\Sigma_{k=1,\ldots W-t}Y_{i,j}[S_j+k,S_j+k+t]$$
$$TC^1Y_{i,j}[S_j+k,S_j+k+t]) \quad \text{ALG. 4}$$

and the output is the value of hr corresponding to the maximal value of the cost function ALG. 4, taking into account the relationship between $D_r$ and hr.

Optionally, there is no transmitted audio and A[ ]=0.

Optionally, the tolerance for calculated heart rate is modified. For example, the definitions above define $D_r$ and example functions for a tolerance of 10%, or $D_r$. Alternative definitions and functions may be written for higher or lower tolerance in the calculated heart rate, such as tolerance of 5% in heart beat per minute, 2% in heart beat per minute, 1% in heart beat per minute, 0.1% in heart beat per minute, and the like.

Optionally, the window for computing heart rate, denoted W, has a value corresponding to the number of samples of two or more heart beats. Optionally, the window for computing heart rate has a value corresponding to the number of samples of between 3 and 12 heart beats.

Optionally, the input signal vector is recorded from an output transducer with standard, off-the-shelf earphones without special hardware requirements.

Optionally, the input signal vector is recorded from an output transducer during subject movement and/or in the presence of background noise.

Optionally, the input signal vector is recorded from an output transducer during playing of an output audio signal through the same output transducer.

Optionally, ALG. 5 finds the pulse rate from the blood pressure signal. The blood pressure signal may be calculated by playing an output signal through the transducer placed inside the ear, denoted by A[ ], record the signal through the same and/or another transducer placed inside the ear, denoted by E[ ], and using an algorithm to estimate the blood pressure signal from E[ ] and A[ ]. The algorithm may exploit the phenomenon that E[ ] contains A[ ] echoed by the ear canal. These echoes are influenced by the frequency response of the ear canal volume, which is in correlation with the blood pressure signal.

For brevity, the following are additionally defined:

E[ ] denotes the audio signal recorded by the transducer;
A[ ] denotes the audio signal played by the client terminal;
$C_t$[ ] denotes the coefficient vector of frequency response of the transducer;
$C_e(i)$[ ] denotes the coefficient vector of frequency response of the ear canal at time frame i;
T[ ] denotes the function between differences of $C_e$ (i)'s and the volume derivative of the ear canal signal; T[ ] is an output of a calibration process, executed in advance.
$D_i$ denotes the derivative of blood pressure signal at time i, and $D_i=-<T, C_e(i+1)-C_e(i)>$; and
BP denotes the blood pressure signal, and $BP(i)=\Sigma_{j=1,\ldots,i} D_j$.

To calculate the blood pressure signal, first divide the signals E[ ] and A[ ] to short consecutive intervals in a length between second/(5*pulse) and second/(50*pulse). Denote the i-th interval by A(i) and E(i). Estimate $C_e$ (i) by:

$$C_e(i)=\text{argmin}\|E(i)-C_t*A(i)+C_e(i)*C_t*A(i)\|^2 \quad \text{ALG. 5}$$

and calculate:

$$D_i=-<T,C_e(i+1)-C_e(i)>$$

where $D_i$ may be an estimation for the derivative of blood pressure signal at time i:

$$BP(t)=\Sigma_{j=1,\ldots,t} D_j$$

Finding the pulse rate from the signal BP may be done using previous methods described herein. The function T[ ] may be a linear approximation of the transformation function between the output signal and the input signal for a particular earphone and/or ear canal. Optionally, T[ ] is an approximation function of order two or more, for example, a quadratic function is used.

Algorithm Description

When the audio played is A[ ] and the audio recorded by the transducer is E[ ], then:

$$E=C_t*A+C_e*C_t*A$$

where $C_t$[ ] may be a short vector of coefficients such that the audio played by the transducer is $C_t*A$. $C_t$ is constant and can be calibrated by recording and playing a sound when the earphone is not inside the ear canal.

$C_e$[ ] is the frequency response vector of the ear canal. When an audio signal X is being played inside the ear, the signal $C_e*X$ is being recorded by the transducer. $C_e$[ ] is a result of X being echoed by the ear canal.

The algorithm may use consecutive short time frames to estimate the frequency response vectors, where $C_e(i)$ may be the vector corresponding to the i-th frame. The volume derivative of the ear canal may be a function of the difference between consecutive time frames. This function, being approximately linear, may estimate the volume derivative of the ear canal at time I, such as $<T,\Delta_i>$, where $\Delta_i=C_e(i+1)-C_e(i)$. Thus the derivative of the blood pressure signal at time i may be $<T,\Delta_i>$. The derivative at each time frame may estimate the blood pressure signal, and specifically the pulse rate.

According to some embodiments of the present invention there are provided computerized methods, for a client terminal to measure temperature using an audio output transducer, such as an earphone speaker. To measure temperature using an audio transducer, the audio transducer may be connected simultaneously to an input mixer and to an output mixer of an audio processing integrated circuit. The output audio signal played by the output transducer and the input audio signal recorded from the output transducer when acting as a microphone may be used to compute the temperature. For example, when earphones worn by a user are connected to a client terminal using a soundcard which allows simultaneous output and input paths to and from the earphones, the body temperature of the user is measured. In this example, a calculation of body temperature is performed using the client terminal. The audio output transducer of an earphone may be used simultaneously to output an output audio signal and to record an audio signal. The audio output signal played by the output transducer may be any audio output signal. For example, the output audio signal is a music signal, voice signal, and the like.

The temperature measured may be the temperature of the surrounding environment of the transducer, which may vary a lot. For example, the temperature measured is the average temperature of the surrounding of the membrane and the average temperature of the surrounding of the back of the output transducer. These two temperatures may be very different, for example, in the case of earphones in which the temperature surrounding the membrane is the temperature of the inner ear of a user, while the surrounding temperature of the back cavity is the ambient temperature of the user's outer ear.

An audio transducer may transmit an audio output signal, denoted A[ ], simultaneously with recording an audio signal, denoted E[ ]. For example, E is an audio signal recording using the output transducer as a microphone, and the recorded signal E includes the recording of the audio output signal, A. The vectors A and E may be used to calculate the temperatures of the front and back of the corresponding output transducer. Optionally, the temperatures of the audio output transducer may be calculated immediately by the client terminal or may be stored, optionally transferred, and calculated at a later time, and optionally at a remote location.

The frequency response between A[ ] and E[ ] may be used to calculate the temperature. The physical principle that allows calculating the front and back temperature of the output transducer may be the previously described frequency response changes as a function of temperature. These frequency response changes may be different for temperature changes of the front and back of the transducer, thereby allowing differentiation between the two temperatures.

For example, reference is now made to an exemplary function for calculating temperature using the frequency response between A[ ] and E[ ]. The frequency response $C_{tf0,tb0}$ is measured at basis temperatures $tb_0$ and $tf_0$ of the back and front of the output transducer respectively. The frequency response $C_{tf0+\Delta,tb0}$ and $C_{tf0,tb0+\Delta}$ are measured at temperatures that are $\Delta$ different from $tf_{0,\Delta}$ of the front of the transducer or $\Delta$ different from $tb_0$ of the back of the transducer and the linear transformation $T_{\Delta,0}$ between $C_{tf0,tb0}$ and $C_{tf0+\Delta,tb0}$ and the linear transformation $T_{0,\Delta}$ between $C_{tf0,tb0}$ and $C_{tf0,tb0+\Delta}$ are thus determined. Since $T_{\Delta,0}$ and $T_{0,\Delta}$ may be the linear transformations corresponding to changes of $\Delta$ of the front or back of the speaker respectively, and we assume they are nearly constant for temperatures close enough to tf0 and tb0, by iteratively applying $T_{\Delta,0}$ and $T_{0,\Delta}$ to $C_{tf0,tb0}$ we may estimate the frequency response at new temperatures $tb_0+k_b\cdot\Delta$ and $tf_0+k_f\Delta$. By reversing this process, a measured frequency response may be used to calculate back and front temperatures that would produce this frequency response.

For example, frequency responses are measured at 25 degrees centigrade for both front and back of the output transducer and found to be flat with −2.0 dB attenuation at 5 kHz. The frequency response measured at 25.5 degrees centigrade for the back of the output transducer may be flat with −2.5 dB attenuation at 5 kHz. The frequency response measured at 25.5 degrees centigrade for the front of the output transducer may be flat with −2.2 dB attenuation at 5 kHz and +0.5 dB attenuation at 3 kHz. The frequency response measured at unknown temperatures $tb_0+k_b\cdot\Delta$ and $tf_0+k_f\Delta$ of the output transducer may be flat with −6.4 dB attenuation at 5 kHz and +6.0 dB attenuation at 3 kHz. By finding the number of times, $k_b$ and $k_f$, the two linear transforms need to be applied, the temperatures for the front and back may be calculated as 37 and 27 degrees centigrade, respectively.

For brevity, the following are additionally defined:

$C_0[N]$ denotes a transducer coefficients vector at baseline temperatures $tf_0, tb_0$ with $tb_0$ being the temperature in the back of the transducer and $tf_0$ being the temperature at the front of the transducer.

$T_{\Delta,0}[N] [N], T_{0,\Delta}[N] [N]$ denotes linear transformations of the transducer coefficient vector such that $T_{\Delta,0}^{k1}(T_{0,\Delta}^{k2}(C_0))$ are the transducer coefficients at temperatures $tb_0+k_1\cdot\Delta$ and $tf_0+k_2\cdot\Delta$ at the back and front respectively, where $\Delta$ is the temperature step used to measure the linear transforms and $k_1$ and $k_2$ are the number of temperature steps. The linear transforms for both the front and back temperatures are applied iteratively $k_1$ and $k_2$ times on $C_0$ to reach the actual measured signal E.

$\|x\|$ denotes the $1^2$ norm of x $x*y$ denotes the convolution of x and y.

tf, tb denote the temperature at the front and back respectively of the output transducer $H_f$, $H_b$ denote heat transfer coefficients of the front and back of the output transducer respectively.

The method may estimate the temperatures tf, tb to be $tb_0+k_1\cdot\Delta$ and $tf_0+k_2\cdot\Delta$, using the function:

$$k_1, k_2 = \mathrm{argmin} \|T_{\Delta,0}^{k1}(T_{0,\Delta}^{k2}(C_0))*A-E\|^2$$

Optionally, tf and tb may be found by solving $D = \mathrm{argmin} \|D*A-E\|^2$ using linear equations of the derivative of D equal to 0, after which we find $k_1, k_2$ such that $k_1, k_2 = \mathrm{argmi} \|T_{\Delta,0}^{k1}(T_{0,\Delta}^{k2}(C_0))-D\|^2$.

Optionally, a calculation of temperatures is performed using two different temperature step resolutions for $T_{\Delta 1}[N] [N]$ and $T_{\Delta 2}[N] [N]$, where $\Delta_2 >> \Delta_1$. In this case D may be calculated as before, and $k_1$, $k_2$ calculated such that $k_1, k_2 = \mathrm{argmin} \|T_{\Delta 1}^{k1}(T_{\Delta A2}^{k2}(C_0))-D\|^2$. The different resolution steps allow better differentiation between the effects of the front and back temperatures on the coefficient vector.

Optionally, the algorithm may use a few sets of basis coefficients. Namely $C_0[N], \ldots, C_s[N]$ which are the transducer coefficients at temperatures $tb_0, \ldots, tb_s$ and $tf_0, \ldots, tf_s$. In this case D may be calculated as before, but tf/tb may be calculated using:

$$tf, tb = \mathrm{argmin} \Sigma_{i=0,\ldots,s} \|T_{\Delta,0}^{(tb-tbi)/\Delta}(T_{0,\Delta}^{(tf-tfi)/\Delta}(C_i))*A-E\|^2$$

which may be calculated by solving linear equations. Optionally, any number of basis temperatures may be used.

Optionally, the temperature is calculated with two or more pairs of linear transformations. For example, $T_{\Delta 1,0}[N] [N]$, $T_{\Delta 1',0}[N] [N]$ and $T_{0,\Delta 2}[N] [N]$ and $T_{0,\Delta 2}[N] [N], T_{0,\Delta 2'}[N] [N]$ such that $\Delta 1' >> \Delta 1$ and $\Delta 2' >> \Delta 2$. In this case D may be calculated as before, but $k_1, k_1', k_2, k_2'$ calculated using:

$$k_1, k_1', k_2, k_2' = \mathrm{argmin} \|T_{\Delta 1',0}^{k1'} \cdot T_{\Delta 1,0}^{k1}(T_{0,\Delta 2'}^{k2'} \cdot T_{0,\Delta 2}^{k2}(C_0))*A-E\|^2$$

Optionally, different basis temperatures and different temperature resolution steps are be used together determine the target temperature.

Optionally, tb and/or tf are calculated at two or more times, and the values extrapolated to a future steady state temperature value. For example, A and E are collected continually and segmented into windows, with a tf and/or tb value calculated for each window. For example, the process may be repeated x times, and the final tf and/or tb is then taken to be the extrapolation of the x intermediate results.

An issue with temperature measurements as described herein may be that the temperature measured is that of the back and front of the transducer, and not the temperature of the inner ear or the environment. It may take the transducers temperature a long time to reach the temperatures of its surrounding. For this reason, the speed of temperature change of the transducer may be used to estimate the temperatures of its surrounding. Optionally, the heat transfer coefficients Hb and Hf are used and if the front and back temperatures are tf, tb and a second later are tf, tb' the surrounding temperatures are $\delta b = Hb \cdot (tb' - tb)$ and $\delta f = Hf \cdot (tf' - tf)$.

Optionally, the final steady state temperatures are extrapolated using an exponential function and heat transfer coefficients.

Figure 5:
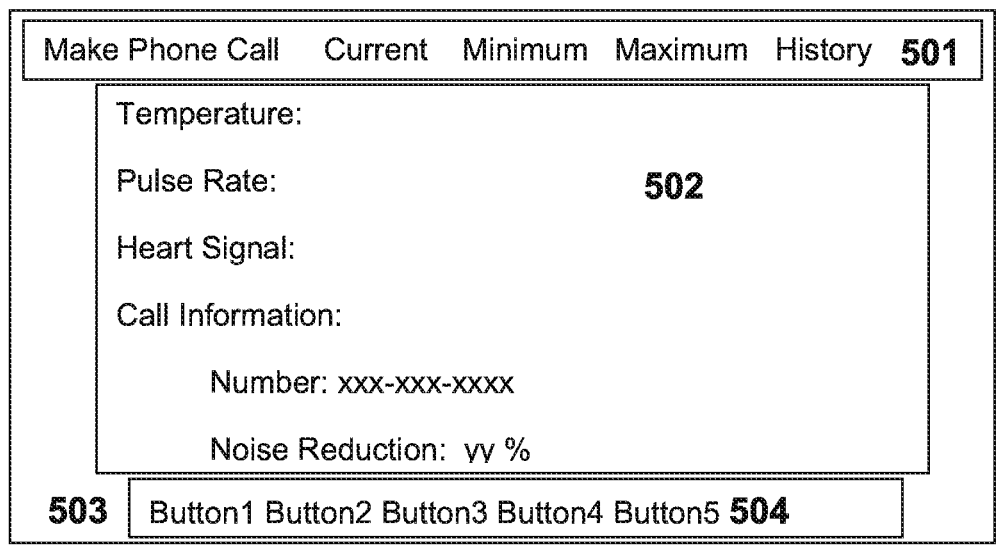
FIG. 5 is a schematic illustration of a user interface to record a signal from an earphone output speaker, compute signals and/or measures data, and outputting the data, according to some embodiments of the invention.

Reference is now made to FIG. 5, which is a schematic illustration of a user interface to record a signal from an earphone output speaker, compute signals and/or measures data, and outputting the data, according to some embodiments of the invention. The user interface may contain a region for a command menu 501. The user interface may contain a region for measurement display 502 including measurements of body temperature, ambient temperature, pulse rate, heart signal, phone information, call information, noise reduction metrics, and the like. The user interface may contain a region for user defined buttons 504. The user interface may be presented on a display of a client terminal 503. For example, the display 503 is the screen of a smartphone, personal computer, laptop, music player, tablet, and the like.

The methods as described above may be used in the fabrication of integrated circuit chips.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant earphone will be developed and the scope of the term earphone is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of presenting a temperature, comprising:
playing an output audio signal to an electro-acoustic transducer;
instructing an audio processing integrated circuit of a client terminal to record an acoustic audio signal that includes the output audio signal that was played by the electro-acoustic transducer, using same said electro-acoustic transducer;
calculating a plurality of temperatures based on a function combining said acoustic audio signal, the output audio signal, and filtration coefficients; and
presenting at least one of said plurality of temperatures.

2. The method of claim 1, wherein said electro-acoustic transducer is a microphone.

3. The method of claim 1, wherein said electro-acoustic transducer is an output speaker of an earphone.

4. The method of claim 1, wherein said electro-acoustic transducer is an external speaker connected to an earphone, and said plurality of temperatures comprises ambient and inner ear temperatures.

5. The method of claim 1, wherein said electro-acoustic transducer is an internal speaker of a client terminal, and said plurality of temperatures comprises ambient and device temperatures.

6. The method of claim 1, wherein said electro-acoustic transducer is located inside an ear canal of a target user during recording of said acoustic audio signal and one of said plurality of temperatures is an inner ear temperature correlated with a body temperature of said target user.

7. The method of claim 1, wherein at least one of said plurality of temperatures is presented to a user through a user interface.

8. The method of claim 1, wherein at least one of said plurality of temperatures is presented to a remote device through an output interface.

9. A non-transitory computer readable medium comprising computer executable instructions adapted to perform actions, the actions comprising:
playing an output audio signal to an electro-acoustic transducer;
instructing an audio processing integrated circuit of a client terminal to record an acoustic audio signal that includes the output signal that was played by the electro-acoustic transducer, using same said electro-acoustic transducer;
calculating a plurality of temperatures based on a function combining said acoustic audio signal, the output audio signal, and filtration coefficients; and
presenting at least one of said plurality of temperatures.

10. The non-transitory computer readable medium of claim 9, wherein said electro-acoustic transducer is an external speaker connected to an earphone, and said plurality of temperatures comprises ambient and inner ear temperatures.

11. The non-transitory computer readable medium of claim 9, wherein said electro-acoustic transducer is an internal speaker of a client terminal, and said plurality of temperatures comprises ambient and device temperatures.

12. The non-transitory computer readable medium of claim 9, wherein said electro-acoustic transducer is located inside an ear canal of a target user during recording of said acoustic audio signal and one of said plurality of temperatures is an inner ear temperature correlated with a body temperature of said target user.

13. The non-transitory computer readable medium of claim 9, wherein at least one of said plurality of temperatures is presented to a user through a user interface.

14. The non-transitory computer readable medium of claim 9, wherein at least one of said plurality of temperatures is presented to a remote device through an output interface.

15. The method of claim 1, wherein calculating the plurality of temperatures based on the function combining said acoustic audio signal, the output audio signal, and filtration coefficients includes determining a difference between the output audio signal and the acoustic audio signal to calculate the plurality of temperatures.

16. The method of claim 1, wherein calculating the plurality of temperatures based on the function combining said acoustic audio signal, the output audio signal, and filtration coefficients includes determining a frequency response between the output audio signal and the acoustic audio signal to calculate the plurality of temperatures.

17. The method of claim 1, wherein the filtration coefficients represent a frequency response of the electro-acoustic transducer.

18. The method of claim 1, wherein the electro-acoustic transducer is simultaneously connected to an input mixer and an output mixer of an audio processing integrated circuit during the playing of the output audio signal and a recording of the acoustic audio signal.

19. The method of claim 1, wherein the plurality of temperatures are temperatures of a surrounding environment of the transducer.

20. The method of claim 1, wherein the plurality of temperatures are temperatures of an inner ear of a user.

21. The non-transitory computer readable medium of claim 9, wherein calculating the plurality of temperatures based on the function combining said acoustic audio signal, the output audio signal, and filtration coefficients includes determining a difference between the output audio signal and the acoustic audio signal to calculate the plurality of temperatures.

22. The non-transitory computer readable medium of claim 9, wherein calculating the plurality of temperatures based on the function combining said acoustic audio signal, the output audio signal, and filtration coefficients includes determining a frequency response between the output audio signal and the acoustic audio signal to calculate the plurality of temperatures.

23. The non-transitory computer readable medium of claim 9, wherein the filtration coefficients represent a frequency response of the electro-acoustic transducer.

24. The non-transitory computer readable medium of claim 9, wherein the electro-acoustic transducer is simultaneously connected to an input mixer and an output mixer of an audio processing integrated circuit during the playing of the output audio signal and a recording of the acoustic audio signal.

25. The non-transitory computer readable medium of claim 9, wherein the plurality of temperatures are temperatures of a surrounding environment of the transducer.

26. The non-transitory computer readable medium of claim 9, wherein the plurality of temperatures are temperatures of an inner ear of a user.

\* \* \* \* \*